(12) United States Patent
Yang

(10) Patent No.: US 11,037,285 B2
(45) Date of Patent: Jun. 15, 2021

(54) MACHINE VISION BASED AUTOMATIC NEEDLE CANNULA INSPECTION SYSTEM AND METHODS OF USE

(71) Applicant: JB MEDICAL, INC., Wujiang (CN)

(72) Inventor: Jibin Yang, Sparta, NJ (US)

(73) Assignee: JB MEDICAL, INC., Suzhou (CN)

( * ) Notice: Subject to any disclaimer, the term of this patent is extended or adjusted under 35 U.S.C. 154(b) by 472 days.

(21) Appl. No.: 15/523,365

(22) PCT Filed: Oct. 15, 2015

(86) PCT No.: PCT/CN2015/091957
§ 371 (c)(1),
(2) Date: Apr. 28, 2017

(87) PCT Pub. No.: WO2016/066017
PCT Pub. Date: May 6, 2016

(65) Prior Publication Data
US 2017/0256049 A1 Sep. 7, 2017

(30) Foreign Application Priority Data
Oct. 31, 2014 (CN) .......................... 201410597857.6

(51) Int. Cl.
*H04N 7/18* (2006.01)
*G06T 7/00* (2017.01)
(Continued)

(52) U.S. Cl.
CPC ............ *G06T 7/0004* (2013.01); *G01B 11/02* (2013.01); *G01N 21/952* (2013.01);
(Continued)

(58) Field of Classification Search
CPC .................................................. G06T 7/0004
(Continued)

(56) References Cited

U.S. PATENT DOCUMENTS 3,929,295 A * 12/1975 Montalbano ........ A61M 5/3278
241/100
4,784,071 A * 11/1988 Sadeh .................. D05B 35/102
112/470.07
(Continued)

FOREIGN PATENT DOCUMENTS

CN 101806752 A 8/2010
CN 101832947 A 9/2010
(Continued)

OTHER PUBLICATIONS

International Patent Application No. PCT/CN2015/091957 filed Oct. 15, 2015 in the name of JB Medical, Inc., 26 pages.
(Continued)

*Primary Examiner* — Leron Beck
(74) *Attorney, Agent, or Firm* — Birch, Stewart, Kolasch & Birch, LLP

(57) ABSTRACT

A machine vision based automatic needle cannula inspection system and methods of use. The system comprises of an inspection and control unit, image capture devices (32, 33), light sources (34, 35, 36, 37), a unit that makes the needle cannula (28) and the image capture device(s) (32, 33) rotate relative to each other, and a rejected part removal unit. By means of rotating the needle cannula (28) and image capture devices (32, 33) relatively, a plurality of images captured along the circumferential direction of the needle cannula are directly saved to a computer, the images are then screened, processed and analyzed to fulfill the automatic inspection of multiple quality and technical parameters of the needle cannula without the need to position the bevel area of cannula tip to a specific direction. Inspection parameters and accuracy can be set at any time, the system can automatically record classification and statistics of passed and rejected needle cannulae for query, and the rejected cannulae are removed automatically at next position. All the functions (Continued)

Figure 1:
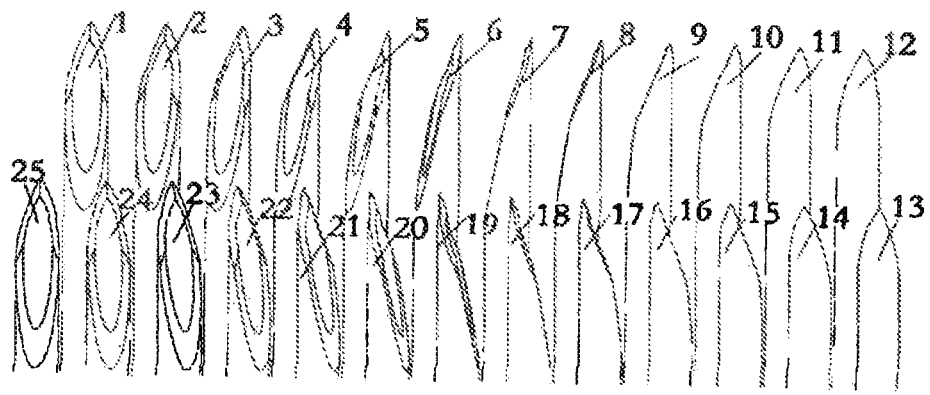

are completed at one work station, and needle cannula tips on both sides can be inspected simultaneously, if needed. Thereby the inspection efficiency and reliability are greatly improved, resulting in extremely extensive application prospects and huge economic values.

11 Claims, 5 Drawing Sheets

(51) Int. Cl.
    *G01B 11/02*     (2006.01)
    *G06T 7/62*     (2017.01)
    *G01N 21/952*     (2006.01)
    *G06T 7/90*     (2017.01)
    *G06T 7/70*     (2017.01)

(52) U.S. Cl.
    CPC .............. *G06T 7/0006* (2013.01); *G06T 7/62* (2017.01); *G06T 7/70* (2017.01); *G06T 7/90* (2017.01); *G06T 2207/10016* (2013.01)

(58) Field of Classification Search
    USPC .......................................................... 348/92
    See application file for complete search history.

(56) References Cited

U.S. PATENT DOCUMENTS

| | | | | |
|---|---|---|---|---|
| 5,601,475 A * | 2/1997 | Stametz | ........... | A61B 17/06066 451/327 |
| 6,115,650 A * | 9/2000 | Demarest | ......... | A61B 17/06004 700/245 |
| 6,355,017 B2 * | 3/2002 | Buttgen | .............. | A61M 5/3202 604/110 |
| 9,545,480 B2 * | 1/2017 | Hunkeler | .............. | A61M 5/002 |
| 2006/0178578 A1 * | 8/2006 | Tribble | ................... | B65B 3/003 600/432 |
| 2008/0269687 A1 * | 10/2008 | Chong | .................... | A61L 15/58 604/180 |
| 2009/0198208 A1 * | 8/2009 | Stavsky | ................ | A61J 1/2096 604/407 |
| 2010/0006602 A1 * | 1/2010 | Giribona | ............... | B01F 9/0016 222/145.5 |
| 2011/0301551 A1 * | 12/2011 | Koehler | .............. | A61M 5/1626 604/263 |
| 2013/0242082 A1 * | 9/2013 | Miller | ...................... | H04N 7/18 348/94 |
| 2014/0114279 A1 * | 4/2014 | Klinghoffer | ........ | A61M 5/1408 604/506 |

FOREIGN PATENT DOCUMENTS

| | | |
|---|---|---|
| CN | 102303017 A | 1/2012 |
| CN | 103134811 A | 6/2013 |
| CN | 104483321 A | 4/2015 |
| JP | 2009092474 A | 4/2009 |
| JP | 2014034461 | 2/2014 |
| WO | 2016066017 A | 5/2016 |

OTHER PUBLICATIONS

International Search Report issued in International Patent Application No. PCT/CN2015/091957 dated Jan. 11, 2016, 5 pages.
Written Opinion of the International Searching Authority issued in International Patent Application No. PCT/CN2015/091957 dated Jan. 11, 2016, 5 pages.
Chinese Patent Application No. 201410597857.6 filed on Oct. 31, 2014 in the name of JB Medical, Inc.

* cited by examiner

MACHINE VISION BASED AUTOMATIC NEEDLE CANNULA INSPECTION SYSTEM AND METHODS OF USE

CROSS-REFERENCE TO RELATED APPLICATIONS

The present application is a National Stage of International Patent Application No. PCT/CN2015/091957, filed Oct. 15, 2015, which claims foreign priority benefits under 35 U.S.C 119 to Chinese Patent Application No. 201410597857.6 (CN) filed 31 Oct. 2014.

TECHNICAL FIELDS

The present invention relates to the technical filed of machine vision based online inspections, especially the machine vision based online automatic inspection of multiple quality and technical parameters of needle cannula and methods of use.

BACKGROUND

The quality of a needle cannula in any medication administration device or system is extremely important. Therefore, ways and means to perform the online automatic inspection of multiple quality and technical parameters of needle cannula have been sought. It is apparent that manual inspection efficiency is very low and the quality is difficult to ensure.

CN102303017B, issued on Dec. 26, 2012, disclosed a machine vision based automatic inspection method to inspect curved steel syringe needles by setting the lateral bending distance of the needle tip as the inspection parameter which can be adjusted according to users' requirements. Camera in the system trigged and controlled by external signal will capture images of online syringe needles. Images will then be transmitted to a computer for image algorithm processing and identifying syringe needles with excessive lateral bending distance than preset parameter as rejected products which will be removed via an external triggered and controlled signal through a specific discharge port.

Figure 2:
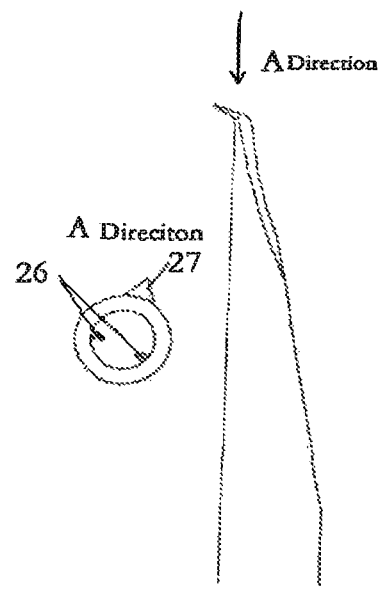

In addition, as shown in FIG. 1, when inspecting needle cannula tip using a machine vision system, the requirement for accurate positioning of needle cannula, especially along the circumferential direction of the cannula, is very high. The bevel area of needle cannula tip must face directly to the image capture device, as shown in the first image of FIG. 1. With the continuous advancement of needle cannula manufacturing technologies, its diameter has become smaller and smaller, fine cannula's diameters are often 0.30 mm (30 G), 0.25 mm (31 G) even 0.20 mm (32 G). These cannulae need to go through necessary processes such as de-buffing and extensive cleaning after tip machining process, resulting in a random distribution of needle cannula bevel's directions. There is no known and effective prior art to position the bevel's direction uniformly without the potential to damage the very fragile tip. Therefore machine vision can not be effectively used for needle tip inspection. People attempted to capture images along cannula's axis (direction A) near the cannula tip, as shown in FIG. 2, thus large burrs (26) and bending tip (27) will show up inside the cannula's inside diameter and outside the cannula's outside diameter. Unfortunately the resolution of this kind of inspection is low, only suitable for cannula with diameter larger than 0.46 mm (26 G) because the smaller the cannula's diameter, the bigger the ratio of the length of cannula's bevels and cannula diameter, and image capture devices also need magnifying lens to capture quality images which will reduce the image depth of field. When cannula's diameter is less than 0.46 mm (26 G), the depth of field of image taking devices with lens is less than the length of cannula's bevels, therefore burs and tip bending will not show up in the image. As a matter of fact, needle cannula of 26 G and bigger is very rarely used nowadays.

INVENTION

The present invention aims to provide an online machine vision based automatic needle cannula inspection system and methods of use as part of an automatic production line. The system and methods have high inspection efficiency and high reliability. Automatic online inspections of multiple quality and technical parameters of needle cannulae and rejected parts removal are completed in one station.

To realize the aforementioned objective, the present invention a machine vision based automatic needle cannula inspection system comprises at least the following:

An inspection and control unit, to establish and realize its synchronized control and information processing with all other units of the automatic inspection system, and one of the following items a, b or c:

a. A needle cannula holding and positioning unit, to separate, position and hold the needle cannula and to be able to keep said needle cannula in position while said needle cannula is driven to rotate; A needle cannula driving unit, to rotate said needle cannula; Fixed image capture device (s), to capture images of rotating needle cannula driven by said needle cannula driving unit while synchronized and controlled by said inspection and control unit;

b. A needle cannula holding, positioning and rotating unit, to separate, position, hold and rotate said needle cannula and to be able to keep said needle cannula in position; Fixed image capture device1(s), to capture images of rotating needle cannula while synchronized and controlled by said inspection and control unit;

c. A fixed needle cannula holding and positioning unit, to separate, position and hold said needle cannula; Image capture device(s) rotating around said needle cannula, to capture images of the said fixed needle cannula while rotating around said needle cannula and synchronized and controlled by the said inspection and control unit;

The present invention a machine vision based automatic needle cannula inspection system, for item a, wherein the said needle cannula holding and positioning unit is a cannula wheel device, or linear stepper tool bars, or a linear stepper belt; Said needle cannula driving unit is a power-driven rotating belt system, or a power-driven rotating wheel, which enables the said fixed image capture device(s) to capture images of rotating needle cannula driven by said needle cannula driving unit while synchronized and controlled by the said inspection and control unit.

The present invention a machine vision based automatic needle cannula inspection system, for item b, wherein said needle cannula holding, positioning and rotating unit is a device that can separate, position, hold and rotate the said needle cannula and to be able to keep said needle cannula in position, so that the said fixed image capture device(s) can capture images of rotating needle cannula while synchronized and controlled by the said inspection and control unit.

The present invention a machine vision based automatic needle cannula inspection system, for item c, wherein the said fixed needle cannula holding and positioning unit is a cannula wheel device, or linear stepper tool bars, or a linear stepper belt, or any device that can individually separate and fix the said needle cannula; Said image capture device(s) rotating around the said needle cannula is a system that rotates around the said needle cannula when driven by power and is capable of keeping the image capture device(s) focused on said needle cannula while capturing images and synchronized and controlled by the said inspection and control unit.

The present invention a machine vision based automatic needle cannula inspection system, for item a, wherein, on both sides of the circumferential edge of the said cannula wheel, or on top of the said linear stepper tool bars or the said linear stepper belt, there are uniformly and symmetrically set teeth, between two adjacent teeth there is a tooth groove or slot where said needle cannula to be inspected is placed in, each tooth groove or slot is placed at most one said needle cannula, said cannula wheel only rotates forward one tooth at a time or the said linear stepper tool bars or the said linear stepper belt only move forward one tooth at a time.

The present invention a machine vision based automatic needle cannula inspection system, for item a, wherein said power-driven rotating belt system or said power-driven rotating wheel is placed above the said cannula wheel or the said linear stepper tool bars or linear stepper belt, forming an engagement area with said cannula wheel or on the said linear stepper tool bars or linear stepper belt in which said power-driven rotating belt or power-driven rotating wheel is pressed onto the said needle cannula near the bottom of tooth grove or slot, when the said belt or wheel is driven to rotate, it will drive the said needle cannula to rotate, said engagement area is a cylindrical area whose diameter is on the circumference of the bottom of said tooth grooves or slots of said cannula wheel, or a plane whose height is the same as the bottom of tooth grooves or slots on said linear stepper tool bars or linear stepper belt, the width of said power-driven rotating belt or power-driven rotating wheel is slightly less than the width of the said engagement area.

The present invention a machine vision based automatic needle cannula inspection system, wherein a plurality of images are captured while said image capture device(s) and said needle cannula rotate relatively for a whole circle.

The present invention a machine vision based automatic needle cannula inspection system defined by above technical scheme can realize the objective of automatic inspection of needle cannulae by capturing images of needle cannula tip area and processing of the images captured using machine vision technologies.

The present invention a machine vision based automatic needle cannula inspection system, wherein a plurality of images are captured while said image capture device(s) and said needle cannula rotate relatively for a whole circle. Said image capture device(s) and said needle cannula can rotate relatively at a constant speed and a plurality of images are captured at equal intervals for a whole circle. Images captured can be processed using machine vision technologies and controlled by the said inspection and control unit to inspect the quality and technical parameters of needle cannulae.

The present invention a machine vision based automatic needle cannula inspection system, wherein said image capture device(s) and said needle cannula can rotate relatively at a constant speed and a plurality of images are captured at equal intervals for a whole circle.

The present invention a machine vision based automatic needle cannula inspection system, wherein said cannula wheel only rotates forward one tooth at a time or the said linear stepper tool bars or the said linear stepper belt only move forward one tooth at a time.

To better position the needle cannula on both sides of said cannula wheel or linear stepper tool bars or linear stepper belt, the present invention a machine vision based automatic needle cannula inspection system, wherein, on both sides of the circumferential edge of the said cannula wheel, or said linear stepper tool bars or the said linear stepper belt, there are teeth, between two adjacent teeth there is a tooth groove or slot, said engagement area with said power-driven rotating belt system or said power-driven rotating wheel is between teeth one both sides.

The present invention a machine vision based automatic needle cannula inspection system, wherein, said teeth, tooth grooves or slots are uniformly and symmetrically set to ensure that needle cannulae will not be bent when pressed and driven to rotate by said power-driven rotating belt system or said power-driven rotating wheel.

As a further preferred embodiment, the present invention a machine vision based automatic needle cannula inspection system, wherein said needle cannula is at the root of said tooth groove or slot, said engagement area with power-driven rotating belt system or said power-driven rotating wheel is the area between the teeth on both sides, said engagement area on said cannula wheel is a cylinder whose diameter is on the circumference of root of teeth on both sides, said engagement area on said linear stepper tool bars or linear stepper belt is a plane coinciding with the plane formed by the root of teeth on both sides.

The present invention a machine vision based automatic needle cannula inspection system, wherein the width of said power-driven rotating belt or power-driven rotating wheel is slightly less than the width of the said engagement area to ensure the sooth operation of said power-driven rotating belt or power-driven rotating wheel.

The present invention a machine vision based automatic needle cannula inspection system, wherein the system uses multithreading techniques.

The present invention a machine vision based automatic needle cannula inspection system, wherein said image capture device(s) can be double image capture devices to inspect both bevel areas at each end simultaneously for needle cannula with bevel areas at both ends.

The present invention a machine vision based automatic needle cannula inspection system further comprises at least one light source electrically connected and controlled by said inspection and control unit.

The present invention a machine vision based automatic needle cannula inspection system further comprises a rejected part removal unit using compressed air to realize simple but reliable rejected parts removal.

The present invention a machine vision based automatic needle cannula inspection system, wherein said inspection and control unit is a computer, said image capture device is at least one camera, said inspection and control unit is connected with said image capture device(s), motors of said needle cannula holding and positioning unit or said needle cannula holding, positioning and rotating unit or said fixed needle cannula holding and positioning unit, and said rejected part removal unit respectively with synchronized control settings.

The present invention a machine vision based automatic needle cannula inspection system, wherein images captured by said image capture device(s) are saved to computer directly, conventional graying, filtering, binarization and rough edge extraction are processed on saved images by said computer for further inspection on related parameters.

As a key element of a preferred embodiment of the present invention a machine vision based automatic needle cannula inspection system, the cannula wheel rotates by steps, and structurally on circumferential edge of the wheel, there are teeth, between two adjacent teeth there is a tooth groove to place a needle cannula to be inspected, and there is a engagement area with power-driven rotating belt system on the circumferential edge of the wheel.

As a further preferred embodiment, on both sides of the circumferential edge of the wheel, there are teeth, between two adjacent teeth there is a tooth groove, and said engagement area with power-driven rotating belt system is between the teeth and grooves on both sides, so that said needle cannula can be positioned on both sides of the circumferential edge of the wheel.

As a further preferred embodiment, said teeth and tooth grooves on both sides of the circumferential edge of the wheel are uniformly and symmetrically set to ensure that when the needle cannulae are driven to rotate at constant speed, said image capture device(s) can capture images at equal interval, so that a more reliable dada is provided for further inspection analyses.

Another substantial part of the present invention, a machine vision based automatic needle cannula inspection method, using the method, a plurality of images are captured along the circumferential direction of said needle cannula for a whole circle by rotating needle cannula relative to image capture device(s), various quality and technical parameters of needle cannula are inspected using machine vision technologies.

The present invention a machine vision based automatic needle cannula inspection method, wherein images captured along the circumference of needle cannula can be continuous and at equal intervals for a whole circle.

The present invention a machine vision based automatic needle cannula inspection method comprises the following steps:
A. Select and adjust said image capture device(s), lenses and light sources based on the dimension of said needle cannula and set parameters such as distance, aperture and exposure time to capture clear images;
B. Set the accuracy and threshold for each inspection parameter;
C. Connected said computer with said image capture device (s), motors of cannula wheel device or linear stepper tool bars or linear stepper belt and said rejected part removal unit respectively with synchronized control settings.

The present invention a machine vision based automatic needle cannula inspection method comprises the following steps in a preferred embodiment:
A. Said cannula wheel step rotates forward, or said linear stepper tool bars or linear stepper belt step moves forward;
B. Each tooth groove or slot of said cannula wheel or linear stepper tool bars or linear stepper belt is placed with one needle cannula;
C. Said cannula wheel or linear stepper tool bars or linear stepper belt pauses when the bevel area of said needle cannula in the tooth groove or slot is within the focus position of said image capture device;
D. Said power-driven rotating belt system or said power-driven rotating wheel above the said cannula wheel or linear stepper tool bars or linear stepper belt automatically presses onto the said needle cannula in the tooth grove or slot, and drive the said needle cannula to rotate;
E. Said computer sends a signal to start said image capture device(s);
F. Under illumination of said light sources, a plurality of images are captured at equal intervals while said image capture device(s) and said needle cannula rotate relatively at a constant speed for a whole circle, said images are saved to said computer, processed with machine vision techniques, and whether the needle cannula passes the inspection is recorded.

The present invention a machine vision based automatic needle cannula inspection method, wherein multithreading techniques and double image capture devices can be used to inspect both bevel areas at each end for needle cannula with bevel areas at both ends simultaneously.

The present invention a machine vision based automatic needle cannula inspection method, wherein said cannula wheel step rotates forward one tooth at a time, or said linear stepper tool bars or linear stepper belt step moves forward one tooth at a time.

The present invention a machine vision based automatic needle cannula inspection method, wherein conventional graying, filtering, binarization and rough edge extraction are processed on saved images.

The present invention a machine vision based automatic needle cannula inspection method comprises further the following step:
G. Rejected needle cannula is blown off by compressed air of the rejected part removal device while qualified needle cannulae will advance with said cannula wheel or linear stepper tool bars or linear stepper belt into the next process.

The present invention a machine vision based automatic needle cannula inspection method comprises further the following step:
H. Upon completion of said needle cannula rotating relative to said image capture device(s) for a full circle and image capture process, said cannula wheel or linear stepper tool bars or linear stepper belt controlled by the computer signal advances one tooth and wait for the computer signal to start the image capture device(s) on next needle cannula.

The present invention a machine vision based automatic needle cannula inspection method, wherein a plurality of images captured on one bevel area of said needle cannula are processed to inspect at least one of the following quality and/or technical parameters:
 (a) Burrs on bevels and needle tip sharpness;
 (b) Inward or outward curved needle tips;
 (c) Accuracy of several bevel angles of needle cannula tip;
 (d) Length of needle cannula.

The present invention a machine vision based automatic needle cannula inspection method, wherein the inspection on needle burrs on bevels and tip sharpness by processing and analyzing a plurality of images captured on one bevel area of said needle cannula comprises the following steps:
 (1) Among all the images captured around a full needle cannula circumference on one tip area, choose the one image with largest bright area; then perform accurate continuous area extraction, contour extraction, curve fitting and ellipse fitting to obtain ideal inner contour, outer contour and burrs;
 (2) When the burr's dimension, if any, exceeds the preset threshold, the needle cannula is disqualified;
 (3) Perform linear fitting of the upper portion of the bright area's outer contour, the two straight lines form an intersection above the needle tip, if the distance between the said intersection and the uppermost point of the bright area exceeds the preset threshold, the needle cannula is disqualified.

The present invention a machine vision based automatic needle cannula inspection method, wherein the inspection on inward or outward curved needle tips by processing and analyzing a plurality of images captured on one bevel area of said needle cannula comprises the following steps:

First identify the image with largest bright area as in previous steps, then count forward or backward a number of images, the number is nearest to one-forth of total number of images, in other wards, choose the image that is approximately 90 or 270 degrees to the image with largest bright area; this image is almost the side view of the needle cannula; perform linear fitting of the left and right vertical lines; if the distance between the top point of the longest vertical line and horizontally the leftmost pixel or rightmost pixel exceeds the preset threshold, the needle cannula has a curved tip and is disqualified.

The present invention a machine vision based automatic needle cannula inspection method, wherein the inspection on accuracy of several bevel angles of needle cannula tip by processing and analyzing a plurality of images captured on one bevel area of said needle cannula comprises the following steps:

Using the same method as in previous steps, perform linear fitting on a few lines in the bevel area, in this embodiment there are 3 bevels, so there are 2 fitting lines, i.e., fitting line 51 for bevel A and fitting line 52 for bevel B, angles formed between the cannula left outer line 49 and fitted lines can be calculated and compared with preset threshold; by processing the image of near 180 degrees to this image, the accuracy of bevel angles on the other side can also be inspected.

The present invention a machine vision based automatic needle cannula inspection method, wherein the needle cannula length can be calculated when both ends of the needle cannula are inspected and the distance between camera A 32 and camera B 33 is calibrated, thus the needle cannula length can be inspected by comparing with preset threshold.

The present invention a machine vision based automatic needle cannula inspection method, wherein the needle cannula length can be calculated when only one end of the needle cannula is inspected, the other end is in a fixed position and the distance between camera and the other end is calibrated, thus the needle cannula length can be inspected by comparing with preset threshold.

The present invention a machine vision based automatic needle cannula inspection method, wherein the system can automatically record classification and statistics of passed and rejected cannulae for query.

The present invention a machine vision based automatic needle cannula inspection method, wherein a plurality of images captured along the circumferential direction of said needle cannula for a whole circle can be used to build a three-dimensional model, with which quality and technical parameters can be inspected.

The present invention has the following beneficial effects:

Using the present invention a machine vision based automatic needle cannula inspection system and method to inspect multiple quality and technical parameters of needle cannula online, inspection parameters and accuracy can be set at any time, the system can automatically record classification and statistics of passed and rejected cannulae for query, and the rejected cannulae can be removed automatically, the system can alarm with sound and light and display images of rejected products. Without the need to position the bevels of cannula tip to a specific direction, the system realizes the first time the automatic inspection of multiple quality and technical parameters of the needle cannula and rejected product removal at one work station. The system can inspect needle cannula at both ends simultaneously, thereby the inspection efficiency and reliability are greatly enhanced. Using the system and method of the present invention, automatic inspection of needle cannula can be realized with a personal computer, industrial camera(s) and light sources, resulting in high cost effective ratio, extremely extensive application prospects and huge economic values.

DRAWINGS

Figure 3:
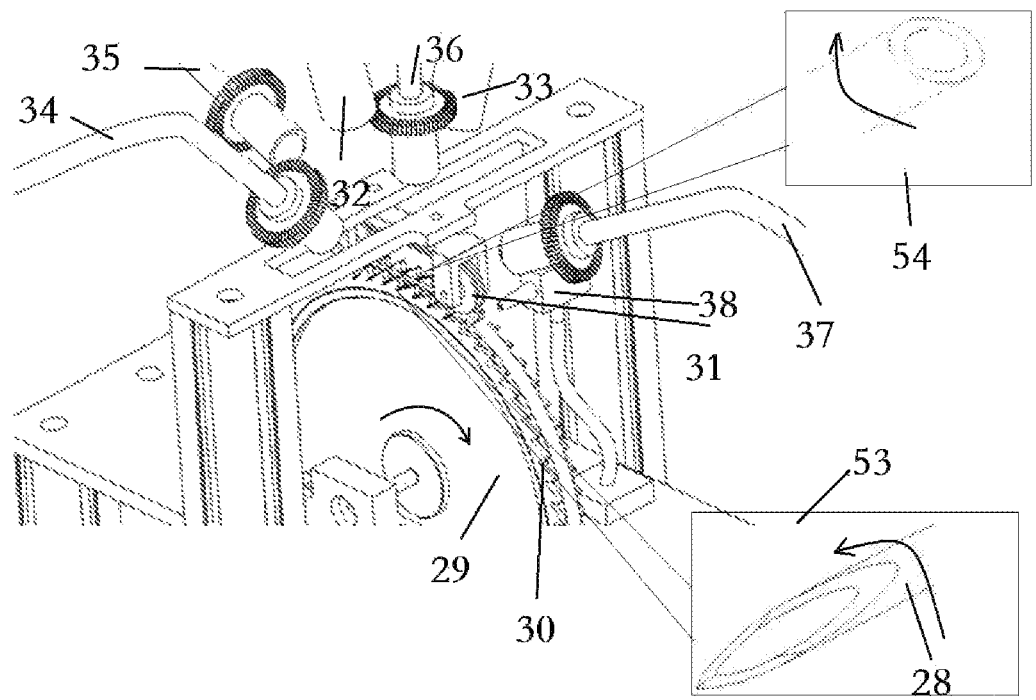
Figure 4:
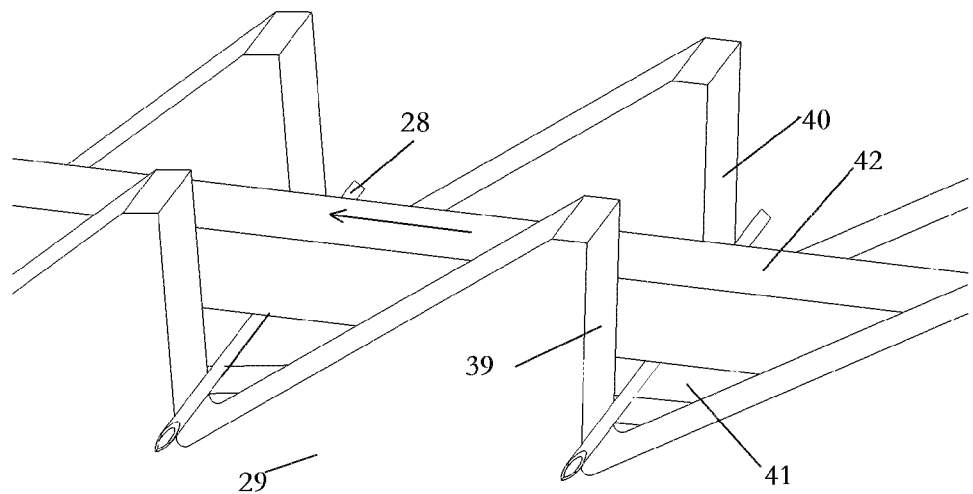
Figure 5:
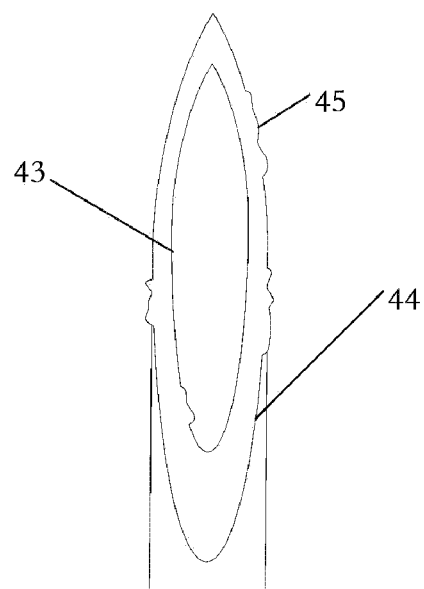
Figure 6:
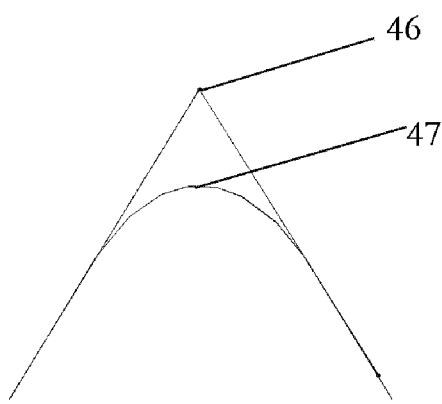
Figure 7:
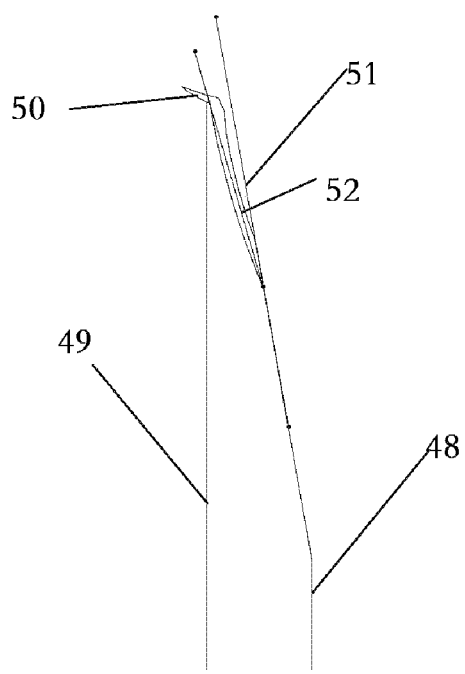
Figure 8:
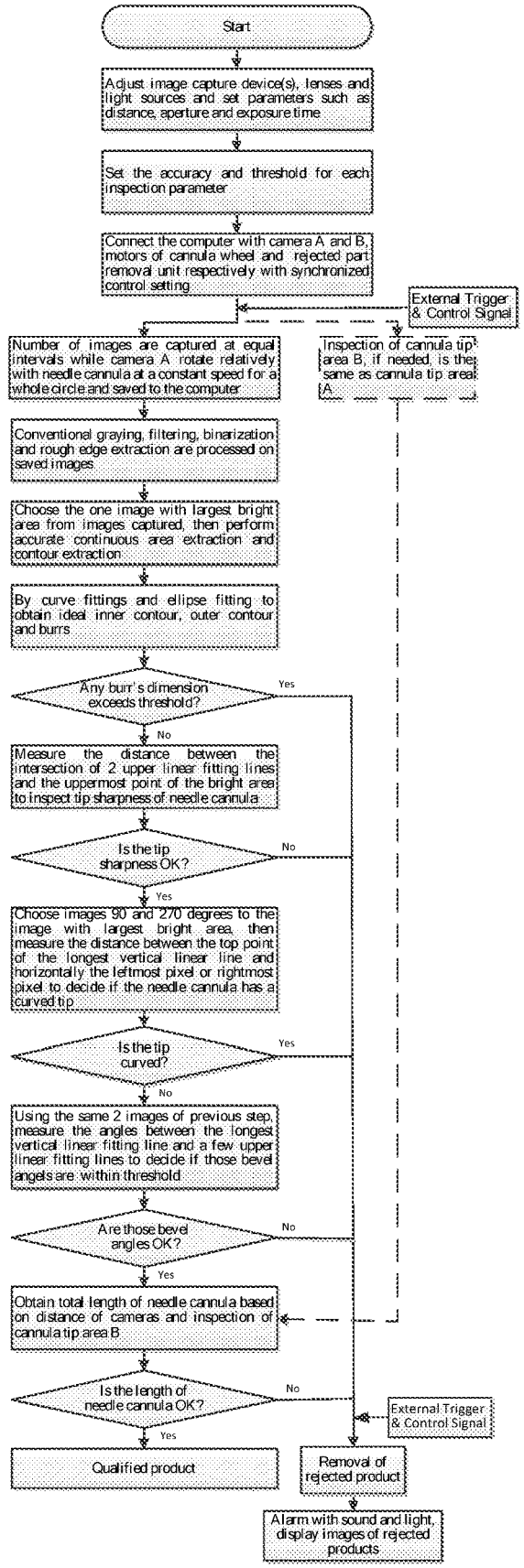

Constituting a part of this application, the accompanying drawings are included to provide a further understanding of the invention, exemplary embodiments of the present invention and the descriptions thereof are used to explain the present invention, and do not constitute improper limitation to the present invention. In the drawings:

FIG. 1 is the side images of a needle cannula tip area at a full revolution or circle FIG. 2 is a schematic view toward the needle tip along the axis of needle cannula FIG. 3 is a preferred embodiment of the system FIG. 4 is on the relationship among the cannula wheel, needle cannula and rotating belt system FIG. 5 is a schematic diagram of the inspection of burrs of a needle cannula tip area FIG. 6 is a schematic diagram of the inspection of needle tip sharpness FIG. 7 is a schematic side view of the needle cannula FIG. 8 is a flow chart of the present invention.

Components in the drawings are labeled as follows:
1-25, side view of 25 images of a needle cannula tip area at equal intervals and a full revolution or circle; 26, burrs at needle cannula tip area; 27, curved needle cannula tips; 28, needle cannula; 29, cannula wheel; 30, tooth grooves; 31, the rotating belt system; 32, camera A; 33, camera B; 34, light source A; 35, light source B; 36, light source C; 37, light sourced D; 38, rejected part removal device using compressed air; 39, tooth groove A; 40, tooth groove B, 41, cylinder; 42, rotating belt; 43, inner contour of needle cannula tip area; 44, outer contour of the needle cannula tip area; 45, burrs; 46, the intersection point of fitting straight lines; 47, uppermost point of needle cannula tip area; 48, right fitting straight line of cannula; 49, left fitting straight line of cannula; 50, curved needle cannula tip; 51, fitting straight line of slope A; 52, fitting straight line of slope B; 53, enlarged view of the needle cannula tip A; 54, enlarged view of the needle cannula tip B The present invention will be described below with reference to a preferred embodiment in conjunction with the drawings.

A Preferred Embodiment

It should be noted that, under the condition of no conflict, embodiments of the present invention and the features of the embodiments can be combined with each other. The present invention will be described below with reference to the drawings and the detailed description in conjunction with the embodiments.

As shown in FIG. 3, the present invention a machine vision based automatic needle cannula inspection system and method, a number of images of needle cannula tip area are captured continuously at equal intervals for a full circle by rotating the needle cannula and the image capture device relatively, multiple quality and technical parameters are inspected through processing and analyzing the images captured using machine vision technologies. After each needle cannula 28 is automatically discharged into the tooth groove 30 of the cannula wheel 29, the cannula wheel pauses when the root of tooth groove 30 is at the top position, the rotating belt system 31 above cannula wheel 29 automatically presses on to the cannula 28 inside the tooth groove 30 and drives the cannula 28 to rotate, the computer sends a signal to start camera A 32 and camera B 33 to capture a number of images at equal intervals and save to the computer under illumination of light source A 34, light source B 35, light source C 36 and light source D 37 when cannula 28 and camera A and Camera B rotates relatively for a full circle, The images are processed using machine vision technologies and results are recorded. rejected parts will be blown away by compressed air of rejected part removal device 38 at rejected parts removal position, qualified needle cannula will advance with the cannula wheel to next process. Meanwhile, at the completion of the needle cannula 28 rotates relatively with camera A 32 and camera B 33 for a full circle, the cannula wheel 29 step advance one tooth after receiving a control signal from the computer indicating the image capture process is completed, awaiting camera A 32 and camera B 33 to receive a signal from the computer to start image capture on next cannula.

As shown in FIG. 4, tooth groove A and tooth groove B are on cannula wheel 29 to position needle cannula 28, cylinder 41 is sandwiched by the tooth groove A and tooth groove B, the outer diameter of cylinder 41 is on the circumference of the bottom of tooth grooves A and B, tooth groove A 39 and tooth grooves B 40 are symmetrically set to ensure that needle cannula is not bent when pressed and driven to rotate by the power-driven rotating belt system. the width of the power-driven rotating belt is slightly less than the inner distance between the tooth groove A and tooth groove B.

When a number of images captured on one bevel area of said needle cannula are processed to inspect at least one of the following quality and/or technical parameters:
(1) Burrs on bevels and needle tip sharpness;
(2) Inward or outward curved needle tips;
(3) Accuracy of several bevel angles of needle cannula tip area;
(4) Length of needle cannula.

The present invention a machine vision based automatic needle cannula inspection method according to a preferred embodiment, comprises the following steps:
(1) Select and adjust said image capture device(s), lenses and light sources based on the dimension of said needle cannula and set parameters such as distance, aperture and exposure time to capture clear images;
(2) Set the accuracy and threshold for each inspection parameter;
(3) Connect the computer with camera A 32 and camera B 33, motors of cannula wheel 29 and rejected part removal unit 38 respectively with synchronized control setting;
(4) Cannula wheel 29 step rotates forward, one tooth at a time, each tooth groove 30 of cannula wheel 29 is automatically placed with one needle cannula, cannula wheel 29 pauses when the bottom of tooth groove 30 is at the upmost position, the rotating belt system 31 above the cannula wheel 29 automatically presses onto the needle cannula 28 in the tooth grove 30 and drive the needle cannula 28 to rotate, a signal sent from the computer starts camera A 32 and camera B 33, under illumination of light source A 34. light source B 35, light source C 36, light source D 37. a number of images are captured at equal intervals while camera A 32 and camera B 33 rotate relatively with needle cannula 28 at a constant speed for a whole circle, the images are saved to the computer and processed with machine vision techniques;
(5) Conventional graying, filtering, binarization and rough edge extraction are processed on saved images.
(6) As shown in FIGS. 5 and 6, when the system performs inspections on needle burrs on bevels and tip sharpness, first choose the one image with largest bright area among all the images captured around a full needle cannula circumference on one tip area, this is the image captured closest to the position when the entire bevel area of the needle cannula is exposed to the camera the most, i.e. position 1 in FIG. 1, then perform accurate continuous area extraction, contour extraction, curve fitting and ellipse fitting to obtain ideal inner contour 43, outer contour 44 and burrs 45, as shown in FIG. 5. When the burr's dimension, if any, exceeds the preset threshold, the needle cannula is disqualified. Then perform linear fitting of the upper portion of the bright area's outer contour, the two straight lines form an intersection 46 above the needle tip, if the distance between the intersection 46 and the uppermost point of the bright area 47 exceeds the preset threshold, the needle cannula is disqualified, as shown in FIG. 6.
(7) As shown in FIG. 7, when the system performs inspections on inward or outward curved needle tips, first identify the image with largest bright area as in step (6), then count forward or backward a number of images, the number is nearest to one-fourth of total number of images, in other wards, choose the image that is approximately 90 or 270 degrees to the image with largest bright area, this image is almost the side view of the needle cannula, equivalent to position 7 and 18 in FIG. 1. Then perform linear fitting of the right and left vertical lines 48 and 49 to confirm the longest vertical line 49, if the distance between the top point of the longest vertical line 49 and horizontally the leftmost pixel or rightmost pixel exceeds the preset threshold, the needle cannula has a curved tip and is disqualified.
(8) As shown in FIG. 7, when the system performs inspections on accuracy of several bevel angles of needle cannula, use the same method as in step (7), perform linear fitting on a few lines in the bevel area, in this embodiment there are 3 bevels, so there are 2 fitting lines, i.e., fitting line 51 for bevel A and fitting line 52 for bevel B, angles formed between the cannula left outer line 49 and fitted lines can be calculated and compared with preset threshold to decide whether the needle cannula is qualified. By processing the image of near 180 degrees to this image, the accuracy of bevel angles on the other side can also be inspected.
(9) If the needle cannula inspected has bevel tip areas at both ends, the same steps (5) to (8) can be used to inspect the other end simultaneously. The length of needle cannula can be calculated when both ends of the needle cannula are inspected and the distance between camera A and camera B is calibrated, thus the needle cannula length can be inspected by comparing with preset threshold. When only one end of the needle cannula is inspected, the other end is in a fixed position and the distance between camera and the other end is calibrated, the needle cannula length can also be inspected by comparing with preset threshold.
(10) The system can automatically record classification and statistics of passed and rejected cannulae for query, rejected needle cannula is blown off by compressed air of the rejected part removal device 38 at rejected part removal position while qualified needle cannulae will advance with cannula wheel into the next process. Meanwhile, upon completion of needle cannula 28 rotating relative to camera A 32 and camera B 33 for a full circle and image capture process, cannula wheel 29 controlled by the computer signal advances one tooth and wait for the computer signal to start camera A 32 and camera B 33 to capture images on next needle cannula.

Besides, images captured along the circumferential direction of a needle cannula for a whole circle can be used to build a three-dimensional model, with which quality and technical parameters can be inspected.

The descriptions above are only preferable embodiments of the present invention, and are not intended to limit the present invention. To one skilled in the field, the present invention may have various changes and variations. Within the spirit and principle of the present invention, all modifications, equivalent replacements, improvements, etc. are intended to be included within the scope of the present invention.

The invention claimed is:

1. A machine vision based automatic needle cannula inspection system comprising:
    an inspection and control unit configured to perform synchronized control and information processing with all other units of the automatic inspection system,
    and one of the following items a, b or c:
    a. a needle cannula holding and positioning unit configured to separate, position and hold the needle cannula and to be able to keep the needle cannula in position while the needle cannula is driven to rotate;
    a needle cannula driving unit configured to rotate the needle cannula; and
    fixed image capture device(s) configured to capture images of rotating needle cannula driven to rotate by the needle cannula driving unit while synchronized and controlled by the inspection and control unit;
    b. a needle cannula holding, positioning and rotating unit configured to separate, position, hold and rotate the needle cannula and to be able to keep the needle cannula in position; and
    fixed image capture device(s) configured to capture images of the needle cannula while the needle cannula is rotating while synchronized and controlled by the inspection and control unit;
    c. a fixed needle cannula holding and positioning unit configured to separate, position and hold the needle cannula; and
    image capture device(s) rotating around the needle cannula, and configured to capture images of the fixed needle cannula while the image capture device(s) is rotating around the needle cannula and synchronized and controlled by the inspection and control unit.

2. The needle cannula inspection system according to claim 1, wherein the needle cannula holding and positioning unit is a cannula wheel device, or linear stepper tool bars, or a linear stepper belt;
    the needle cannula driving unit is a power-driven rotating belt system, or a power-driven rotating wheel, which enables the fixed image capture device(s) to capture images of the rotating needle cannula driven by the needle cannula driving unit while synchronized and controlled by the inspection and control unit.

3. The needle cannula inspection system according to claim 1, wherein the needle cannula holding, positioning and rotating unit is a device that can separate, position, hold and rotate the needle cannula and to be able to keep the needle cannula in position, so that the fixed image capture device(s) can capture images of the rotating needle cannula while synchronized and controlled by the-inspection and control unit.

4. The needle cannula inspection system according to claim 1, wherein
    the fixed needle cannula holding and positioning unit is a cannula wheel device, or linear stepper tool bars, or a linear stepper belt, or any device that can individually separate and fix the needle cannula;
    the image capture device(s) rotating around the needle cannula is a system that rotates around the needle cannula when driven by power and is capable of keeping the image capture device(s) focused on the needle cannula while capturing images and synchronized and controlled by the inspection and control unit.

5. The needle cannula inspection system according to claim 2, wherein, on both sides of a circumferential edge of the cannula wheel, or on top of the linear stepper tool bars or the linear stepper belt, there are uniformly and symmetrically set teeth, between two adjacent teeth there is a tooth groove or slot in which the needle cannula to be inspected is placed, each tooth groove or slot receives at most one needle cannula, the cannula wheel only rotates forward one tooth at a time or the linear stepper tool bars or the linear stepper belt only move forward one tooth at a time.

6. The needle cannula inspection system according to claim 5, wherein the power-driven rotating belt system or the power-driven rotating wheel is placed above the cannula wheel or the linear stepper tool bars or the linear stepper belt, forming an engagement area with the cannula wheel or on the linear stepper tool bars or the linear stepper belt in which the power-driven rotating belt or power-driven rotating wheel is pressed onto the needle cannula near the bottom of the tooth groove or slot, when the belt or wheel is driven to rotate, it will drive the needle cannula to rotate, the engagement area is a cylindrical area whose diameter is on a circumference of the bottom of the tooth grooves or slots of the cannula wheel, or a plane whose height is the same as the bottom of the tooth grooves or slots on the linear stepper tool bars or the linear stepper belt, the width of the power-driven rotating belt or the power-driven rotating wheel is slightly less than the width of the-engagement area.

7. The needle cannula inspection system according to claim 1, wherein a plurality of images are captured while the image capture device(s) and the needle cannula rotate relatively for a whole circle.

8. The needle cannula inspection system according to claim 7, wherein the image capture device(s) and the needle cannula rotate relatively at a constant speed and a plurality of images are captured at equal intervals for a whole circle.

9. The needle cannula inspection system according to claim 1, wherein the image capture device(s) are double image capture devices.

10. The needle cannula inspection system according to claim 1, further comprising a rejected part removal unit.

11. The needle cannula inspection system according to claim 10, wherein the inspection and control unit is a computer, the image capture device(s) is at least one camera, the inspection and control unit is connected with the image capture device(s), motors of the needle cannula holding and positioning unit or the needle cannula holding, positioning and rotating unit or the fixed needle cannula holding and positioning unit, and the rejected part removal unit respectively with synchronized control settings.

* * * * *